United States Patent
Kivijarvi et al.

(10) Patent No.: US 9,874,535 B2
(45) Date of Patent: Jan. 23, 2018

(54) MOISTURE METER FOR DETERMINING THE MOISTURE CONTENT OF PARTICULATE MATERIAL

(71) Applicant: Farmcomp Oy, Tuusula (FI)

(72) Inventors: Janne Kivijarvi, Espoo (FI); Jere Keskiaho, Vantaa (FI); Johannes Hyrsky, Espoo (FI)

(73) Assignee: Farmcomp Oy, Tuusula (FI)

( * ) Notice: Subject to any disclaimer, the term of this patent is extended or adjusted under 35 U.S.C. 154(b) by 0 days.

(21) Appl. No.: 15/280,413

(22) Filed: Sep. 29, 2016

(65) Prior Publication Data

US 2017/0016842 A1   Jan. 19, 2017

Related U.S. Application Data

(63) Continuation of application No. 13/832,264, filed on Mar. 15, 2013, now Pat. No. 9,459,225.

(30) Foreign Application Priority Data

Jan. 29, 2013 (FI) ...................................... 20135083

(51) Int. Cl.
*G01N 25/56* (2006.01)
*G01N 27/22* (2006.01)
(Continued)

(52) U.S. Cl.
CPC ........... *G01N 27/223* (2013.01); *G01N 19/10* (2013.01); *G01N 27/226* (2013.01); *G01N 22/04* (2013.01);
(Continued)

(58) Field of Classification Search
CPC ................................................... G01N 27/226
See application file for complete search history.

(56) References Cited

U.S. PATENT DOCUMENTS 2,042,444 A * 5/1936 Marriott, Jr. .............. B03B 5/50
209/462
2,054,476 A 9/1936 Derry et al.
(Continued)

FOREIGN PATENT DOCUMENTS

| WO | 85/00427 A1 | 1/1985 |
| WO | 0014552 A1 | 3/2000 |
| WO | 2011036342 A1 | 3/2011 |

OTHER PUBLICATIONS

Office Action and Search Report from the National Board of Patents and Registration of Finland relating to Finnish Patent Application No. 20135083 dated Sep. 26, 2013.
(Continued)

*Primary Examiner* — R. A. Smith
*Assistant Examiner* — Herbert K Roberts
(74) *Attorney, Agent, or Firm* — Calfee, Halter & Griswold LLP

(57) ABSTRACT

A moisture meter for determining the moisture content of particulate material is provided. The moisture meter comprises a frame part, a space, a measuring cup disposed within said space for receiving a sample of the particulate material which moisture is to be measured, and moisture measuring means. The moisture meter comprises a swiping means for removing at least partly a part of a sample of particulate material which moisture is to be measured, which part of the sample of particulate material extends out of the inner space of the measuring cup through the open end of the measuring cup. The swiping means are movably attached to the frame part for movement in a swiping path where a swiping member of the swiping means is configured to move essentially along the open end of the measuring cup.

20 Claims, 6 Drawing Sheets

(51) Int. Cl.
    *G01N 19/10* (2006.01)
    *G01N 22/04* (2006.01)
    *G01N 5/02* (2006.01)
    *G01N 9/36* (2006.01)
    *G01N 27/04* (2006.01)
    *G01N 27/60* (2006.01)

(52) U.S. Cl.
    CPC ............ *G01N 25/56* (2013.01); *G01N 27/048* (2013.01); *G01N 27/605* (2013.01)

(56) References Cited

U.S. PATENT DOCUMENTS

| | | | | |
|---|---|---|---|---|
| 2,090,525 | A * | 8/1937 | Carrier | A01C 7/06 111/70 |
| 2,422,742 | A * | 6/1947 | Odessey | G01N 27/223 131/908 |
| 2,542,928 | A * | 2/1951 | Kimball | G01N 27/223 324/668 |
| 2,933,220 | A * | 4/1960 | Harker | B65B 1/363 131/112 |
| 3,051,894 | A * | 8/1962 | Fathauer | G01N 27/223 324/668 |
| 3,068,404 | A * | 12/1962 | Moore | G01N 27/048 324/450 |
| 3,427,537 | A * | 2/1969 | Osborne | G01N 27/043 324/694 |
| 3,482,162 | A * | 12/1969 | Wochnowski | A24B 9/00 131/304 |
| 3,559,052 | A * | 1/1971 | Fathauer | G01N 27/223 324/115 |
| 4,050,016 | A * | 9/1977 | Marsh | G01N 27/223 324/668 |
| 4,106,535 | A * | 8/1978 | Davis | E04C 2/36 141/125 |
| 4,107,599 | A | 8/1978 | Preikschat | |
| 4,121,151 | A | 10/1978 | Funk et al. | |
| 4,193,116 | A | 3/1980 | Funk | |
| 4,462,250 | A * | 7/1984 | Stuart | G01N 27/223 324/670 |
| 4,584,522 | A * | 4/1986 | Varela | G01N 27/223 324/667 |
| 5,126,679 | A | 6/1992 | Spry | |
| 5,253,512 | A | 10/1993 | Le Gigan | |
| 5,493,229 | A * | 2/1996 | McMahon | G01N 27/223 324/664 |
| 5,767,685 | A | 6/1998 | Walker | |
| 6,147,503 | A * | 11/2000 | Nelson | G01N 22/04 324/637 |
| 6,413,850 | B1 * | 7/2002 | Ooroku | H01L 24/11 257/E21.508 |
| 2003/0033862 | A1 | 2/2003 | McElhaney et al. | |
| 2004/0189284 | A1 | 9/2004 | Haubold et al. | |
| 2005/0172874 | A1 * | 8/2005 | Bellefroid | A01C 7/102 111/177 |
| 2006/0013279 | A1 | 1/2006 | Funk | |
| 2006/0046801 | A1 * | 3/2006 | Argetsinger | A01D 41/127 460/59 |
| 2007/0095425 | A1 * | 5/2007 | Hashiba | B65B 37/20 141/248 |
| 2011/0086684 | A1 | 4/2011 | Luellen et al. | |

OTHER PUBLICATIONS

Office Action from the Finnish Patent and Registration Office relating to Finnish Patent Application No. 20135083 dated Feb. 9, 2015.

* cited by examiner

MOISTURE METER FOR DETERMINING THE MOISTURE CONTENT OF PARTICULATE MATERIAL

RELATED APPLICATIONS

This application is a continuation of U.S. patent application Ser. No. 13/832,264, filed on Mar. 15, 2013, now U.S. Pat. No. 9,459,225 issued on Oct. 4, 2016, and claims the benefit of, and priority to Finland Patent Application Number 20135083, filed on Jan. 29, 2013. Both of which are fully incorporated herein by reference.

TECHNICAL FIELD

The invention relates to a moisture meter for determining the moisture content of particulate material. By particulate material is meant for example, but not excluding other particulate materials, grain in ungrounded state and in ground state.

Electrical moisture measuring methods employed most frequently in measuring the moisture content of granular material are based either on measurement of resistance in which the effect of moisture on the resistance of the material being examined is observed, on measurement of capacitance in which the moisture alters the dielectric constant and consequently the capacitance of the pick-up, or on impedance measurement in which the effect of moisture both on the resistance and the capacitance of the pick-up is observed.

In all said measuring modes a sample must be used, in order to gain an accurate moisture content figure for the material under examination, which prior to the measuring event has been brought into a given state, which must be repeatable at different times of measuring. This may be done e.g. by measurement of bulk density, or by pressing the sample against the measuring electrodes with a known force.

Publication WO 85/00427 presents a moisture meter.

BACKGROUND OF THE INVENTION

The object of the invention is to provide an improved moisture meter which is capable of repeatably providing a standardized sample of particulate material having essentially the same volume.

SUMMARY

The moisture meter comprises a swiping means for removing at least partly a part of a sample of particulate material whose moisture is to be measured and which has been poured into the inner space of a measuring cup through the open end of the measuring cup, which part of the sample of particulate material extends out of the inner space of the measuring cup through the open end of the measuring cup. The swiping means being movably attached to a frame part for movement in a swiping path where a swiping member of the swiping means is configured to move essentially along the open end of the measuring cup.

The volume of the inner space of the measuring cup can be considered to be defined by a bottom wall, a cylindrical side wall and an imaginary top wall at the open end of the measuring cup. The swiping means is movably attached to the frame part for movement in a swiping path where a swiping member of the swiping means is configured to move essentially along an imaginary top wall at the open end of the measuring cup so that the volume of the sample will have essentially the volume of the measuring cup.

BRIEF DESCRIPTION OF THE DRAWINGS

These and other features and advantages of the present invention will become better understood with regard to the following written description and the following drawings.

DETAILED DESCRIPTION

Figure 1:
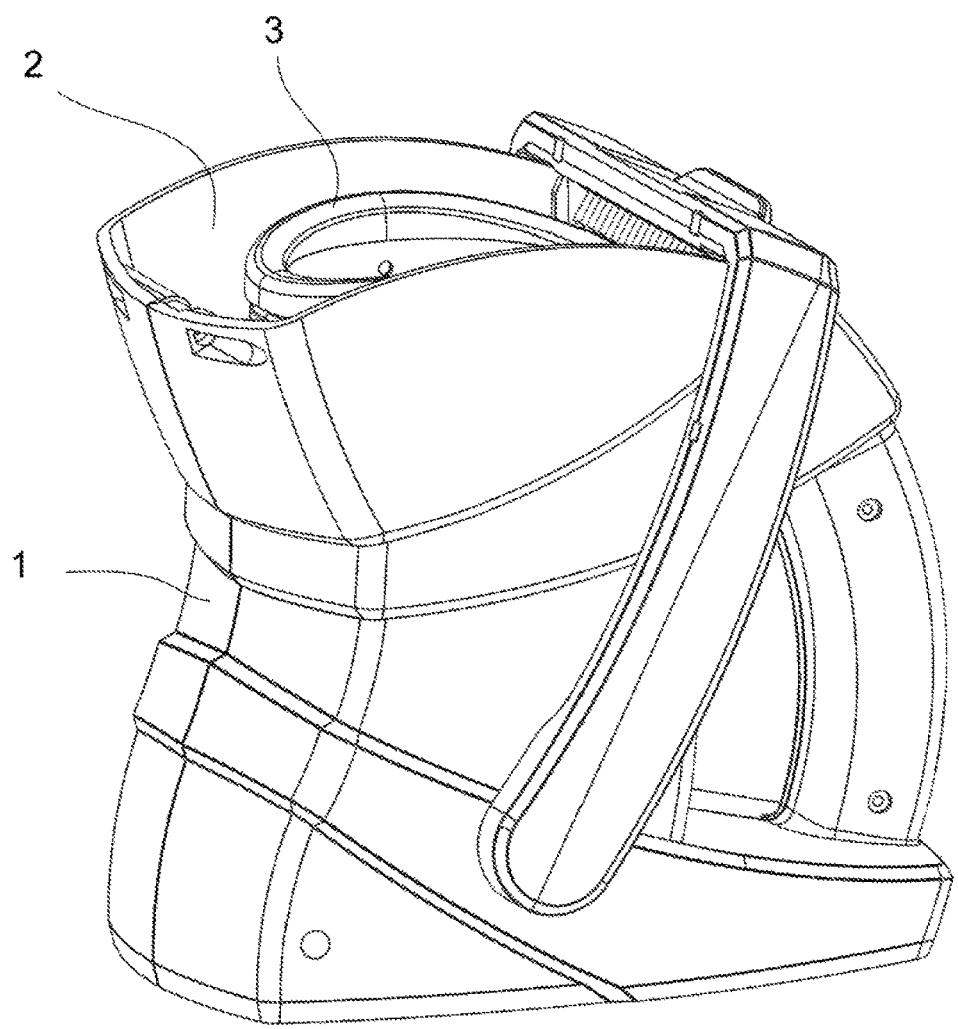
FIG. 1 shows an embodiment of the moisture meter.
Figure 2:
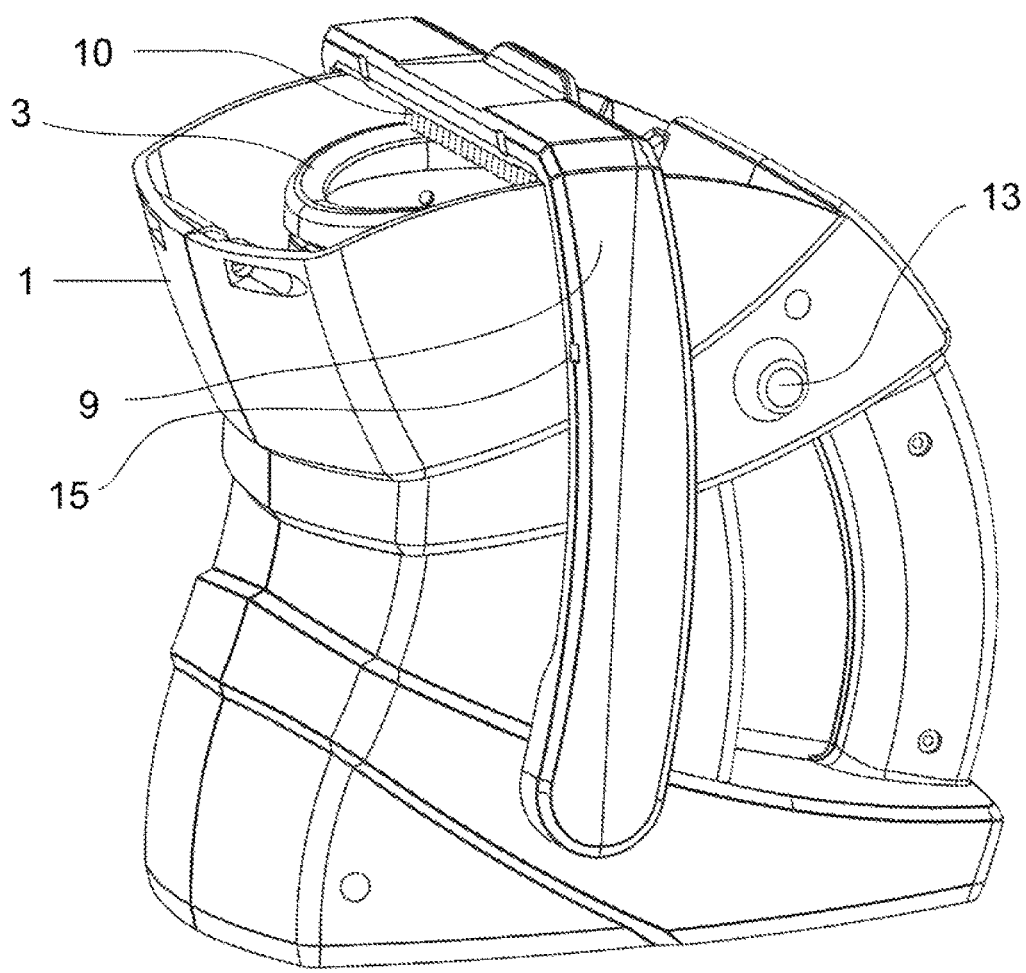
FIG. 2 shows the moisture meter shown in FIG. 1 in a stage where the swiping means have been moved along the open end of the measuring cup in the swiping path.
Figure 3:
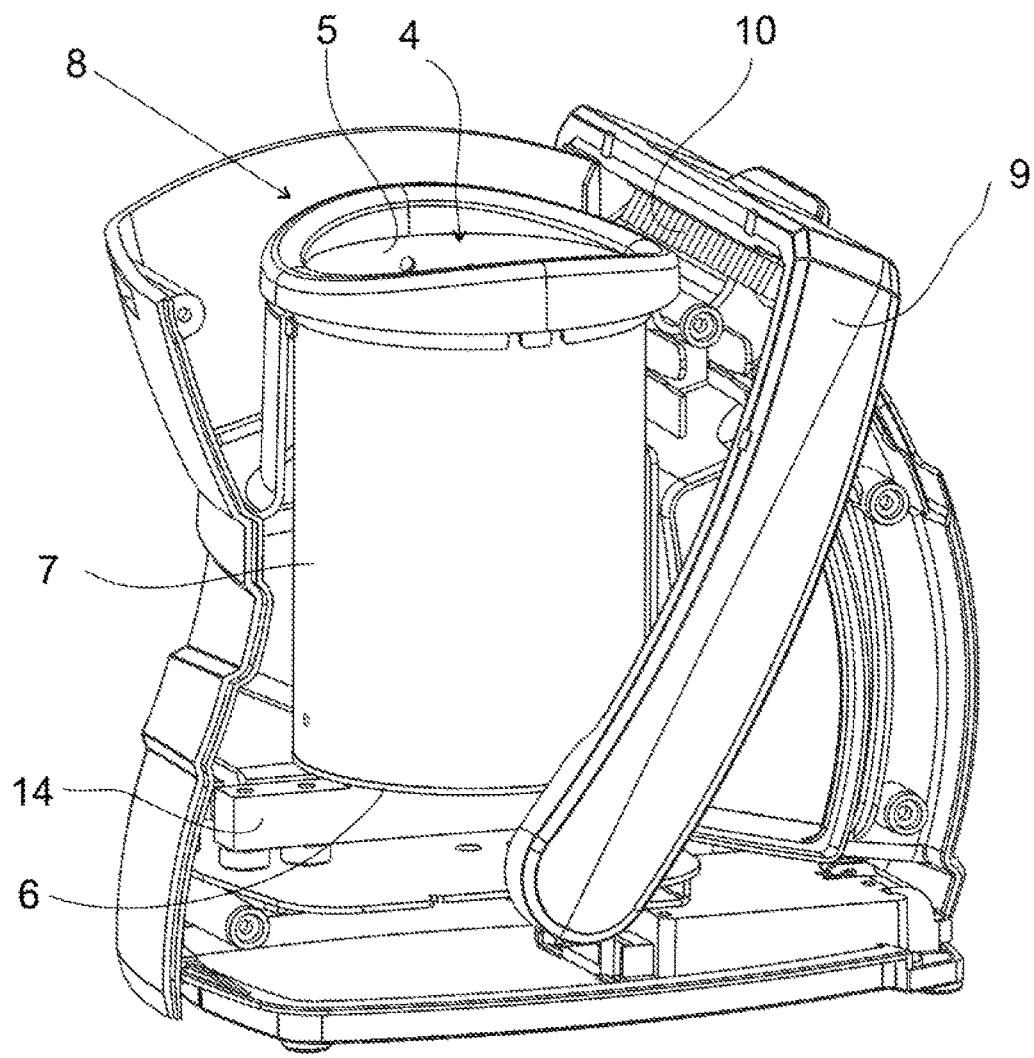
FIG. 3 shows the moisture meter shown in FIG. 1 in partly disassembled stage.
Figure 4:
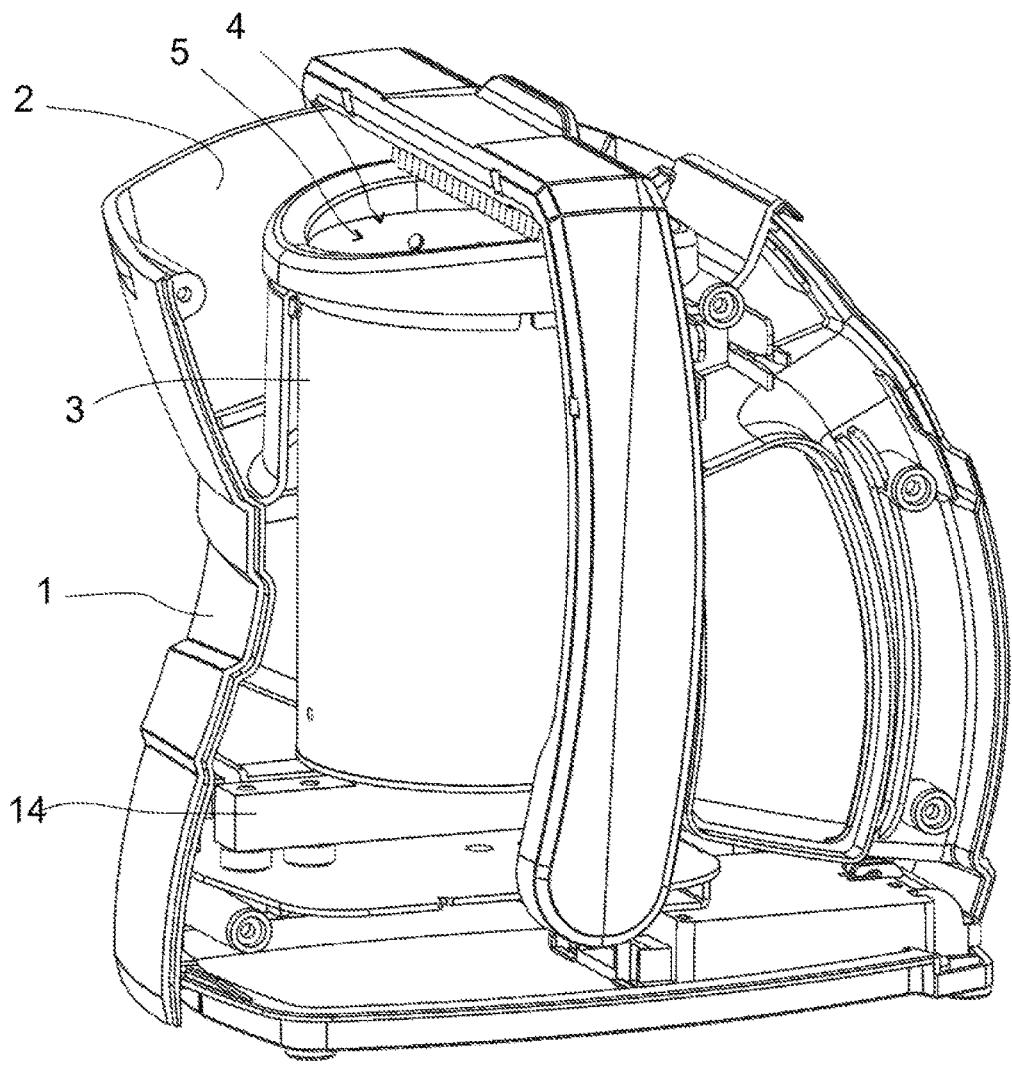
FIG. 4 shows the moisture meter shown in FIG. 3 in partly disassembled stage, where the swiping means have been moved along the open end of the measuring cup in the swiping path.

The Figures show a moisture meter for determining the moisture content of particulate material. The moisture meter comprises a frame part 1. The moisture meter comprises a space 2 defined by said frame part 1.

The moisture meter comprises a measuring cup 3 disposed within said space 2 for receiving a sample of the particulate material (not shown in the drawings) whose moisture is to be measured, wherein measuring cup 3 has an open end 4 through which particulate material whose moisture is to be measured is to be poured and an inner space 5 having a given volume.

The moisture meter comprises moisture measuring means for measuring the moisture content of a sample of the particulate material received in the measuring cup 3.

Said moisture measuring means for measuring the moisture content of a sample of the particulate material received in the measuring cup 3 may, as known to those skilled in the art, be formed so that in said moisture meter said measuring cup 3 being a capacitor of which the impedance is proportional to the moisture content and quantity of a sample of the particulate material received in the measuring cup 3. Alternatively the moisture measuring means may for example be optical moisture measuring means for measuring the moisture content of a sample of the particulate material received in the measuring cup 3.

The moisture meter comprises a swiping means 9 for removing at least partly a part of a sample of particulate material whose moisture is to be measured and which has been poured into the inner space of the measuring cup 3 through the open end of the measuring cup 3, which part of the sample of particulate material extends out of the inner space of the measuring cup 3 through the open end of the measuring cup 3. The swiping means 9 being movably attached to the frame part 1 for movement in a swiping path where a swiping member 10 of the swiping means 9 is configured to move essentially along the open end of the measuring cup 3.

The volume of the inner space of the measuring cup 3 can be considered to be defined by a bottom wall 6, a cylindrical side wall 7 and an imaginary top wall 8 at the open end of the measuring cup 3. The swiping means 9 is movably attached to the frame part 1 for movement in a swiping path where a swiping member 10 of the swiping means 9 is configured to move essentially along the imaginary top wall at the open end of the measuring cup 3 so that the volume of the sample will have essentially the volume of the measuring cup 3. The swiping means 9 may be manually operable.

The measuring cup 3 is preferably, but not necessarily, supported by a scales means (not shown in the drawings) on the frame part 1 of the moisture meter. Said scales means may comprise a load cell 14 arranged between the frame part 1 of the moisture meter and the measuring cup 3 to measure the weight of the particulate material that has been poured into the measuring cup 3. The moisture meter may be arranged to indicate directly the bulk density of the sample of particulate material.

The moisture meter comprises preferably, but not necessarily, a temperature sensing element (not shown in the drawings) that has been arranged to project from the wall such as from the bottom wall 6 of the measuring cup 3 into the sample of particulate material that has been poured into the measuring cup 3.

The moisture comprises preferably, but not necessarily, a temperature sensing element which has been arranged to push from the wall such as from a cylindrical side wall 7 of the measuring cup 3 into the sample of particulate material that has been poured into the measuring cup 3.

In the moisture meter shown in the Figures, the swiping means 9 comprises two elongate members 11 pivotably attached at opposite sides of the frame part 1 and having said swiping member 10 arranged between said two elongate members for moving said swiping member 10 in said swiping path.

Figure 5:
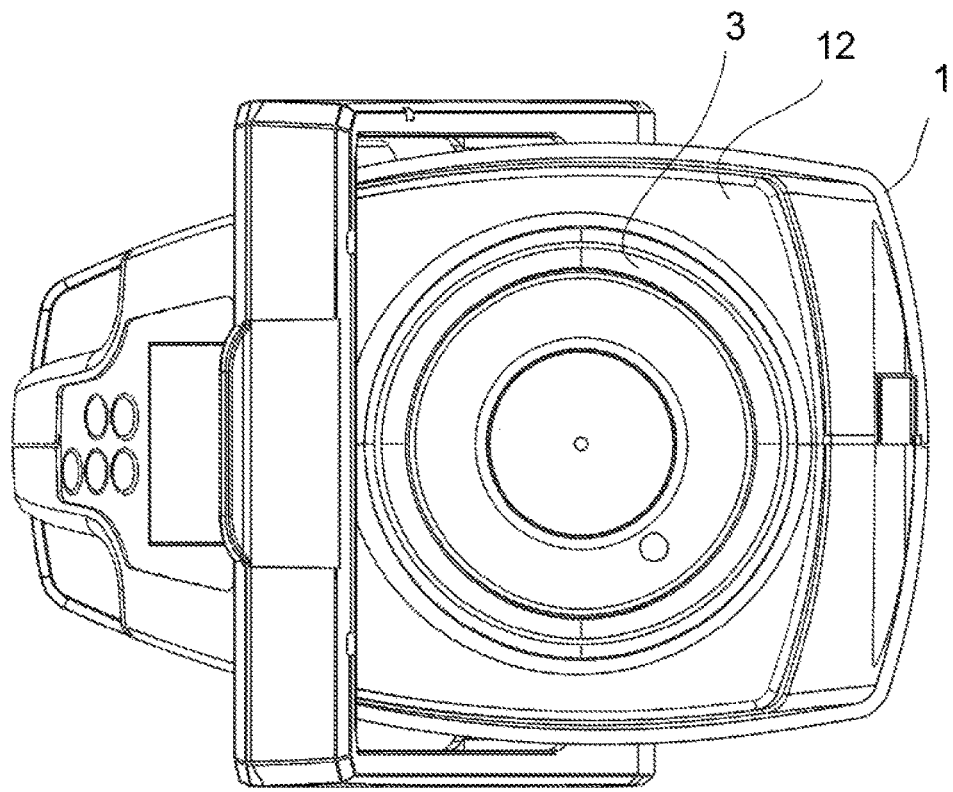
FIG. 5 shows the moisture meter shown in FIG. 1 as seen from above.
Figure 6:
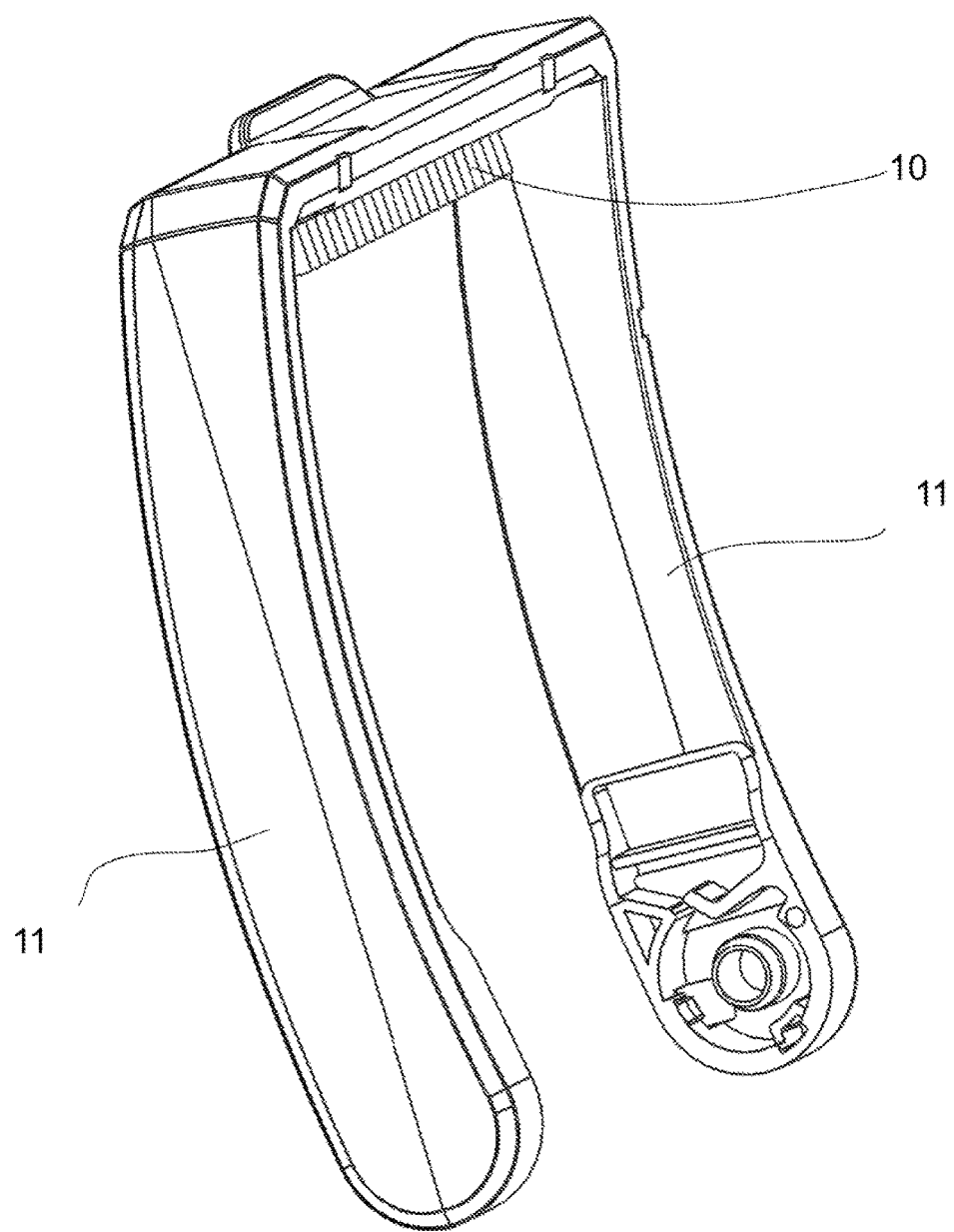
FIG. 6 shows the swiping means of the moisture meter shown in FIG. 1.

In the moisture meter shown in the Figures, the moisture meter is provided with a receiving vessel 12 at least partly, in FIG. 5 completely, surrounding the measuring cup 3 in the frame part 1 for receiving particulate material removed by the swiping means 9.

In the moisture meter shown in the Figures, the swiping means 9 is functionally connected to the moisture measuring means by a sensing means 13 sensing that the swiping member 10 has been moved at least partly in said swiping path along the opening of the measuring cup 3. In the moisture meter shown in the Figures, the sensing means 13 comprises a Hall effect sensor located within the frame part 1 and a magnet 15 located in the elongate member 11 of the swiping means 9.

In the moisture meter shown in the Figures, the swiping member 10 of the swiping means 9 is in the form of a brush. The swiping member 10 of the swiping means 9 could alternatively comprise another form of flexible member or elastic member. Alternatively, the swiping means 9 can be made at least partly flexible or at least partly elastic. The purpose of the flexibility or the elasticity is to prevent large kernels, grains or similar from getting stuck during swiping.

In the moisture meter shown in the Figures, the measuring cup 3 has a cylindrical configuration.

The moisture meter is preferably, but not necessarily, a portable moisture meter.

While the present invention has been illustrated by the description of embodiments thereof and while the embodiments have been described in considerable detail, it is not the intention of the applicant to restrict or in any way limit the scope of the appended claims to such detail. Additional advantages and modifications will readily appear to those skilled in the art. Moreover, elements described with one embodiment may be readily adapted for use with other embodiments. Therefore, the invention, in its broader aspects, is not limited to the specific details, the representative apparatus and illustrative examples shown and described. Accordingly, departures may be made from such details without departing from the spirit or scope of the applicant's general inventive concept.

We claim:

1. A portable moisture meter for determining a moisture content of a particulate material, comprising:
    a housing having a bottom and one or more sides that form an enclosure;
    a first handle on the housing for holding the portable moisture meter;
    a measuring cup located within the enclosure for receiving a sample of the particulate material whose moisture content is to be measured, the measuring cup having a bottom and one or more walls;
    a moisture measuring sensor;
    a display;
    a swiping member pivotally mounted to the housing at a point below the top of the measuring cup that travels along a set path to remove particulate material that is located above the top of the measuring cup;
    wherein the moisture of the sample is measured while the sample is in the cup and after the swiping member has removed portions of the sample which are disposed outside of the inner space of the measuring cup.

2. The moisture meter according to claim 1, wherein the moisture measuring means comprises a capacitor which corresponds to the measuring cup, and the moisture measuring means determines the moisture content of the sample at least in part by determining an impedance of the capacitor.

3. The moisture meter according to claim 2, further comprising a scale disposed in the frame space underneath the measuring cup to determine a weight of the measuring cup as it contains the sample.

4. The moisture meter according to claim 3, wherein the scale comprises a load cell.

5. The moisture meter according to claim 1, wherein the moisture meter determines a bulk density of the sample of particulate material.

6. The moisture meter according to claim 1, further comprising a temperature sensor extending upwardly from a bottom of the measuring cup into the inner space as it contains the sample.

7. The moisture meter according to claim 1, further comprising a temperature sensor extending inwardly from a side wall of the measuring cup into the inner space as it contains the sample.

8. The moisture meter according to claim 1, further comprising two elongated members pivotably attached at opposite sides of the housing, and the swiping member extends between the two elongated members.

9. The moisture meter according to claim 1, wherein the measuring cup comprises a cylindrical configuration.

10. The moisture meter according to claim 1, further comprising a sensor which determines that the swiping member has been moved at least partly along the sweeping path.

11. The moisture meter according to claim 10, wherein the sensor comprises a Hall effect sensor disposed on the frame to detect a magnet that moves with the swiping member.

12. The moisture meter according to claim 1, wherein the swiping member is manually operable.

13. A portable moisture meter for determining a moisture content of a particulate material, comprising:
    a housing having a floor and one or more walls having an opening at the top;

the housing having a handle for holding the portable moisture meter;

wherein the portable moisture meter is configured so that a user can hold the portable moisture meter with one hand;

a measuring cup disposed within housing for receiving a sample of the particulate material;

a moisture measuring sensor; and a swiping member pivotably mounted to the housing at a point below the top of the measuring cup and configured to move in a swiping path along the open end of the measuring cup;

wherein the moisture of the sample is measured while the sample is in the cup and after the swiping member has removed portions of the sample which are disposed outside of the inner space of the measuring cup.

14. The moisture meter according to claim 13, wherein the moisture measuring means comprises a capacitor which corresponds to the measuring cup, and the moisture measuring means determines the moisture content of the sample at least in part by determining an impedance of the capacitor.

15. The moisture meter according to claim 13, further comprising two elongated members pivotably attached at opposite sides of the frame, and the swiping member extends between the two elongated members.

16. The moisture meter according to claim 13, further comprising a sensor which determines that the swiping member has been moved at least partly along the sweeping path.

17. The moisture meter according to claim 16, wherein the sensor comprises a Hall effect sensor disposed on the frame to detect a magnet that moves with the swiping member.

18. The moisture meter according to claim 13, wherein the swiping member is manually operable.

19. A portable moisture meter for determining a moisture content of a particulate material, comprising:

a housing having a bottom and one or more sides;

a handle on the housing for holding the portable moisture meter;

a measuring cup located within the housing for receiving a sample of the particulate material whose moisture content is to be measured, the measuring cup having a bottom and one or more walls;

a moisture meter; and a swiping member pivotally mounted to the housing at a point below the top of the measuring cup that travels along a set path to remove particulate material that is located above the top of the measuring cup;

wherein the swiping member comprises a brush;

a space between the measuring cup and the housing configured to allow particulate material removed by the swiping member fall through so that the particulate material is retained in the housing;

wherein the moisture of the sample is measured while the sample is in the cup and after the swiping member has removed portions of the sample which are disposed outside of the inner space of the measuring cup.

20. The moisture meter according to claim 19 further comprising a display.

* * * * *